(12) United States Patent
Gerold

(10) Patent No.: US 8,915,953 B2
(45) Date of Patent: Dec. 23, 2014

(54) IMPLANT MADE OF A BIODEGRADABLE MAGNESIUM ALLOY

(75) Inventor: Bodo Gerold, Zellingen (DE)

(73) Assignee: Biotronik VI Patent AG, Baar (CH)

(*) Notice: Subject to any disclaimer, the term of this patent is extended or adjusted under 35 U.S.C. 154(b) by 580 days.

(21) Appl. No.: 12/566,312

(22) Filed: Sep. 24, 2009

(65) Prior Publication Data
US 2010/0082092 A1 Apr. 1, 2010

(30) Foreign Application Priority Data
Sep. 30, 2008 (EP) .................................. 08165463

(51) Int. Cl.
*A61F 2/06* (2013.01)

(52) U.S. Cl.
USPC ......................................... 623/1.15; 420/406

(58) Field of Classification Search
USPC ...................... 623/1.15; 420/406; 148/420
IPC .................. C22C 23/06; B22F 2998/10; A61L 31/148, 31/022
See application file for complete search history.

(56) References Cited

U.S. PATENT DOCUMENTS

| 4,401,621 A | 8/1983 | Unsworth et al. |
| 2006/0052864 A1* | 3/2006 | Harder et al. ................. 623/1.38 |
| 2007/0191708 A1 | 8/2007 | Gerold et al. |
| 2008/0033531 A1* | 2/2008 | Barthel et al. ................ 623/1.15 |

FOREIGN PATENT DOCUMENTS

| DE | 103 61 942 A1 | 7/2005 |
| EP | 1 419 793 A1 | 10/2003 |
| EP | 1 419 793 B1 | 10/2003 |
| EP | 1 600 179 A2 | 5/2005 |
| EP | 1 632 255 A2 | 8/2005 |
| EP | 1 842 507 A1 | 10/2007 |

OTHER PUBLICATIONS

European search report for priority application EP 08165463.4, Jan. 21, 2009.

* cited by examiner

*Primary Examiner* — Weiping Zhu
(74) *Attorney, Agent, or Firm* — Wagenknecht IP Law Group PC

(57) ABSTRACT

An implant made in total or in parts of a biodegradable magnesium alloy consisting of Y: 2.0-6.0% by weight, Nd: 1.5-4.5% by weight, Gd: 0-4.0% by weight, Dy: 0-4.0% by weight, Er: 0-4.0% by weight, Zr: 0.1-1.0% by weight, Li: 0-0.2% by weight, Al: 0-0.3% by weight, under the condition that a) a total content of Er, Gd and Dy is in the range of 0.5-4.0% by weight and b) a total content of Nd, Er, Gd and Dy is in the range of 2.0-5.5% by weight, the balance being magnesium and incidental impurities up to a total of 0.3% by weight.

8 Claims, 2 Drawing Sheets

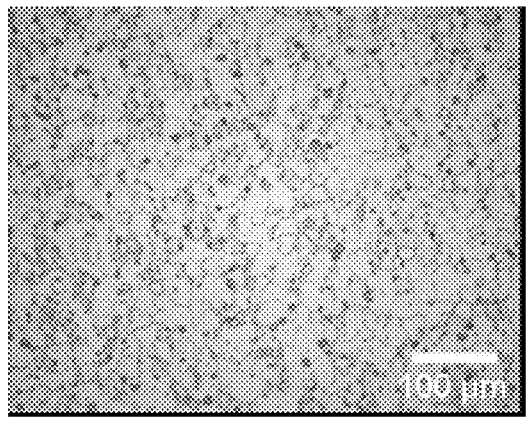 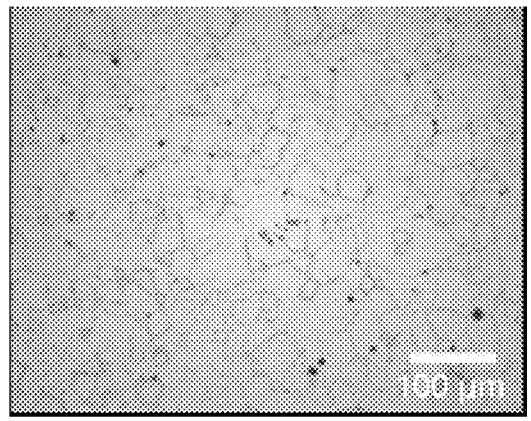
FIG. 1A　　　　　　　　　　FIG. 1B
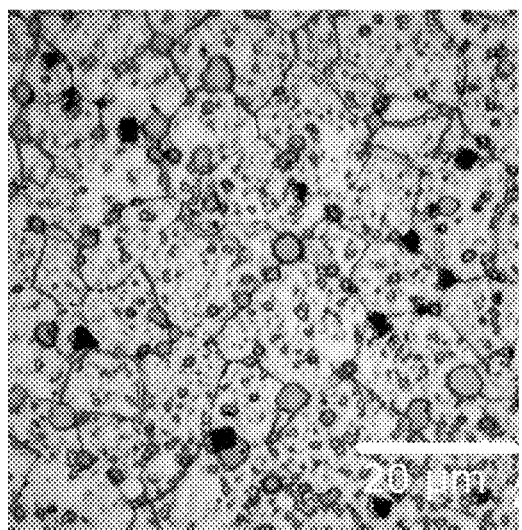 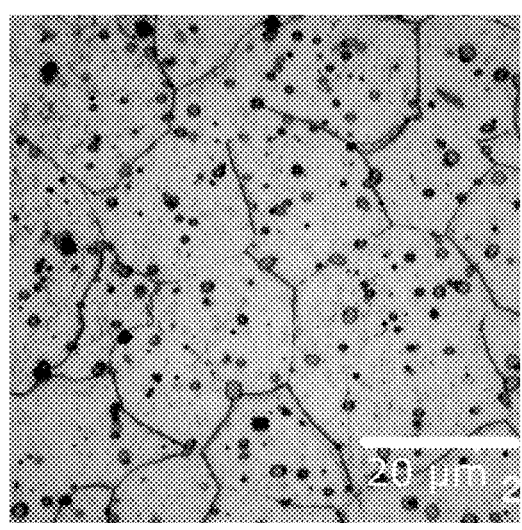
FIG. 2A　　　　　　　　　　FIG. 2B

IMPLANT MADE OF A BIODEGRADABLE MAGNESIUM ALLOY

CROSS REFERENCE TO RELATED APPLICATIONS

This invention claims benefit of priority to Europe patent application EP 08165463.4, filed on Sep. 30, 2008; the contents of which are herein incorporated by reference in their entirety.

FIELD OF THE INVENTION

The present invention relates to implants made of a biodegradable magnesium alloy.

BACKGROUND OF THE INVENTION

Medical implants for greatly varying uses are known in the art. A shared goal in the implementation of modern medical implants is high biocompatibility, i.e., a high degree of tissue compatibility of the medical product inserted into the body. Frequently, only a temporary presence of the implant in the body is necessary to fulfil the medical purpose. Implants made of materials which do not degrade in the body are to be removed again, because rejection reactions of the body may occur in long term even with highly biocompatible permanent materials.

One approach for avoiding additional surgical intervention is to form the implant entirely or in major parts from a biodegradable (or biocorrodible) material. The term biodegradation as used herewith is understood as the sum of microbial procedures or processes solely caused by the presence of bodily media, which result in a gradual degradation of the structure comprising the material. At a specific time, the implant, or at least the part of the implant which comprises the biodegradable material, loses its mechanical integrity. The degradation products are mainly resorbed by the body, although small residues being in general tolerable.

Biodegradable materials have been developed, inter alia, on the basis of polymers of synthetic nature or natural origin. Because of the material properties, but particularly also because of the degradation products of the synthetic polymers, the use of biodegradable polymers is still significantly limited. Thus, for example, orthopedic implants must frequently withstand high mechanical strains and vascular implants, e.g., stents, must meet very special requirements for modulus of elasticity, brittleness, and moldability depending on their design.

One promising attempted achievement provides the use of biodegradable metal alloys. For example, it is suggested in German Patent Application No. 197 31 021 A1 to form medical implants from a metallic material whose main component is to be selected from the group of alkali metals, alkaline earth metals, iron, zinc, and aluminium. Alloys based on magnesium, iron, and zinc are described as especially suitable. Secondary components of the alloys may be manganese, cobalt, nickel, chromium, copper, cadmium, lead, tin, thorium, zirconium, silver, gold, palladium, platinum, silicon, calcium, lithium, aluminium, zinc, and iron.

The use of a biodegradable magnesium alloy having a proportion of magnesium greater than 90% by weight, yttrium 3.7-5.5% by weight, rare earth metals 1.5-4.4% by weight, and the remainder less than 1% by weight is known from European Patent 1 419 793 B1. The material disclosed therein is in particular suitable for producing stents.

Another intravascular implant is described in European Patent Application 1 842 507 A1, wherein the implant is made of a magnesium alloy including gadolinium and the magnesium alloy is being free of yttrium.

Stents made of a biodegradable magnesium alloy are already in clinical trails. In particular, the yttrium (W) and rare earth elements (E) containing magnesium alloy ELEKTRON WE43 (U.S. Pat. No. 4,401,621) of Magnesium Elektron, UK, has been investigated, wherein a content of yttrium is about 4% by weight and a content of rare earth metals (RE) is about 3% by weight. The following abbreviations are often used: RE=rare earth elements, LRE=light rare earth elements (La—Pm) and HRE=heavy rare earth elements (Sm—Lu).

However, it was found that the alloys respond to thermo-mechanical treatments. Although these types of WE alloys originally were designed for high temperature applications where high creep strength was required, it was now found that dramatic changes in the microstructure occurred during processing with repetitive deformation and heat treatment cycles. These changes in the microstructure are responsible for high scrap rates during production and inhomogeneous properties of seamless tubes and therefore in the final product. As a consequence, mechanical properties are affected harmful. Especially, the tensile properties of drawn tubes in the process of manufacturing stents are deteriorated and fractures appear during processing. In addition, a large scatter of the mechanical properties especially the elongation at fracture (early fractures of the tubes below yield strength during tensile testing) was found in the final tube. Finally, the in vivo degradation of the stent is too fast and too inhomogeneous and therefore the biocompatibility may be worsted by inflammation process caused by a tissue overload of the degradation products.

The use of mixtures of light rare earth elements (LRE; La, Ce, Pr, Nd) and heavy rare earth metals (HRE: elements of the periodic table: Sm, Eu, Gd, Tb, Dy, Ho, Er, Tm, Yb and Lu) in commercially available magnesium alloys such as WE43 rather than pure alloying elements reduced the costs and it has been demonstrated that the formation of additional precipitates of these elements beside the main precipitates based on Y and Nd further enhance the high temperature strength of the material [King et al, 59$^{th}$ Annual World Magnesium Conference, 2005, p. 15ff]. It could therefore be postulated the HRE containing precipitates are more stable against growth at higher temperatures because of the significantly slower diffusion rate of these elements compared to Y and Nd. Therefore they contribute substantially to the high temperature strength of WE alloys (particle hardening effect).

However, it now has been found that these HRE precipitates are causing problems when the material is used in biomedical applications, such as vascular implants (e.g. stents) or in orthopaedic implants. The HRE intermetallic particles adversely affect the thermo-mechanical processability of alloys. For example, manufacturing vascular prostheses like stents made of metallic materials usually starts from drawn seamless tubes made of the material. The production of such seamless tubes is usually an alternating process of cold deformation by drawing and subsequent thermal treatments to restore the deformability and ductility, respectively. During the mechanical deformation steps intermetallic particles cause problems because they usually have significant higher hardness than the surrounding matrix. This leads to crack formation in the vicinity of the particles and therefore to defects in the (semi-finished) parts which reduces their usability in terms of further processing by drawing and also as final parts for production of stents.

Intermetallic precipitates also adversely affect the recrystallization behaviour during heat treatments for restoring the plasticity. Impurities are known to affect grain boundary mobility strongly, depending on segregation and mobility. Further, not only the volume failures (precipitates) in the microstructure but also point failures (foreign atoms=all alloying elements) and especially RE atoms contribute to this adverse effect.

Surprisingly it now has been found that precipitation still happens to occur although the temperature regime is high enough that one would expect dissolution of all existing particles. This indicates that intermetallic phases predominantly formed with LRE cannot be dissolved during usual recrystallization heat treatment (300 to 525° C.) of the specific alloys. As a consequence, the ductility for further deformation processes or service cannot be restored sufficiently.

SUMMARY OF THE INVENTION

An aim of this invention is to overcome or to at least lower one or more of the above mentioned problems. There is a demand for a biodegradable Mg alloy having improved processability and, if applicable, improved mechanical properties of the material, such as strength, ductility and strain hardening. In particular, in case of that the implant is a stent a scaffolding strength of the final device as well as the tube drawing properties of the material should be improved.

A further aspect of the invention may be to enhance the corrosion resistance of the material, more specifically, to slow the degradation, to fasten the formation of a protective conversion layer, and to lessen the hydrogen evolution. In case of a stent, enhancing the corrosion resistance will lengthen the time wherein the implant can provide sufficient scaffolding ability in vivo.

Another aspect of the invention may be to enhance the biocompatibility of the material by avoiding toxic components in the alloy or the corrosion products.

One or more of the above mentioned aspects can be achieved by the implant of the present invention. The inventive implant is made in total or in parts of a biodegradable magnesium alloy consisting of:
Y: 2.0-6.0% by weight
Nd: 1.5-4.5% by weight
Gd: 0-4.0% by weight
Dy: 0-4.0% by weight
Er: 0-4.0% by weight
Zr: 0.1-1.0% by weight
Li: 0-0.2% by weight
Al: 0-0.3% by weight
under the condition that
   a) a total content of Er, Gd and Dy is in the range of 0.5-4.0% by weight and
   b) a total content of Nd, Er, Gd and Dy is in the range of 2.0-5.5% by weight,
the balance being magnesium and incidental impurities up to a total of 0.3% by weight.

The use of the inventive Mg—Y—(Nd-)HRE-Zr alloy for manufacturing an implant causes an improvement in processability, an increase in corrosion resistance and biocompatibility compared to conventional magnesium alloys, especially WE alloys such as WE43 or WE54.

Recrystallization, i.e. the ability to form new unstrained grains, is beneficial in restoring ductility to material, which has been strained, for example by extrusion, rolling and drawing. Recrystallization allows material to be restrained to achieve further deformation. Recrystallization is often achieved by heating the alloy between processing steps. If recrystallization temperature can be lowered, the extent of elevated temperature annealing steps can be reduced, and forming of the material can be improved.

It is well recognised that one of the factors which affects recrystallization is the purity of the material; an example being the effect of copper content in aluminium alloys compared with zone refined aluminium [Vandermeer et al., Proc. Symposium on the recovery an recrystallization of metals, New York, TMS AIME, 1962, p. 211]. It may be expected therefore, that improving the purity of Mg—Y—(Nd-)HRE-Zr alloys, by for example, reducing low levels of LRE and HRE would reduce the recrystallisation temperature. However, for magnesium alloys containing RE elements, it has been reported that RE elements increase the recrystallisation temperature. This fact may be related to increased activation energy of recrystallisation. Furthermore, it was observed that the recrystallisation temperature is in general increased in correspondence with the solubility of the RE elements in magnesium, i.e. the more soluble the RE, the higher is the recrystallisation temperature [Rokhlin, Magnesium Alloys containing Rare Earth Metals, 2003, p. 143ff].

Lorimer et al., Materials Science Forum, Vols. 488 to 489, 2005, p. 99 ff, propose that in WE43 alloy, recrystallisation can occur at second phase particles and Particle Simulated Nucleation (PSN) is a mechanism of recrystallisation.

From the above it can be assumed that the direction of teaching for Mg—Y—(Nd-)HRE-Zr type alloys is that generation of RE particles could be beneficial to recrystallisation, but also that increasing RE content (particularly soluble RE) would increase recrystallisation temperature, except for small amounts, where no difference in recrystallisation would be expected.

The presence of particles in Mg—Y—(Nd-)HRE-Zr can be related to any of the constituent elements. Of particular interest to this invention, are the HRE and LRE constituents. WE43 type alloys typically contain 1% RE, which can consist of HRE elements such Sm Eu, Gd, Dy, Er, Yb and LRE elements such as La, Ce and Pr. For example, WE43 manufactured by Magnesium Elektron is composed of Y 3.7-4.3%, RE 2.4-4.4%, Zr 0.4% min and balance magnesium, wherein RE stands for Nd 2.0-2.5% and the remainder being RE elements. Thus, LRE and HRE are present in Mg—Y-RE-Zr alloys of the art. Y and Nd are the elements, which improve strength by precipitation hardening. This relies on the fact that these alloy constituents are in a state of supersaturation and can subsequently be brought out of solution in a controlled manner during ageing (typically at temperatures in the range 200 to 250° C.). The precipitates desired for strength are small in size and could not be readily resolved by optical microscopy. Additional precipitates are also generated which are coarse and readily observed optically as particles. These are usually rich in Nd. These coarse particles are brittle, and may be expected to reduce formability and ductility of the material.

The solubility of RE in magnesium varies considerably: see Table 1.

TABLE 1

Solid solubility of various LRE and HRE in magnesium

| Atomic number | Element | Solid solubility at various temperatures (weight %) | | |
|---|---|---|---|---|
| | | 200° C. | 400° C. | 500° C. |
| 68 | Er | 16 | 23 | 28 |
| 66 | Dy | 10 | 17.8 | 22.5 |

TABLE 1-continued

Solid solubility of various LRE and HRE in magnesium

| Atomic | | Solid solubility at various temperatures (weight %) | | |
|---|---|---|---|---|
| number | Element | 200° C. | 400° C. | 500° C. |
| 64 | Gd | 3.8 | 11.5 | 19.2 |
| 70 | Yb | 2.5 | 4.8 | 8 |
| 62 | Sm | 0.4 | 1.8 | 4.3 |
| 58 | Ce | 0.04 | 0.08 | 0.26 |
| 59 | Pr | 0.01 | 0.2 | 0.6 |
| 60 | Nd | 0.08 | 0.7 | 2.2 |
| 57 | La | — | 0.01 | 0.03 |

From the above, it may be expected to one skilled in the art, that the volume of coarse particles present would be primarily related to the Nd content, due to the low solid solubility of this element.

It now has been discovered however, that by restricting the remaining RE—without changing the Nd or the overall RE content compared to conventional WE43 alloys—to either Er, Gd or Dy of the HRE group or a mixture of these elements, that the volume of coarse Nd rich particles is significantly reduced. This is unexpected, particularly when one considers that the solubility of other HRE elements such as Yb and Sm would be expected to be retained in solution and not contribute to coarse particles. Only La is insoluble in the range of compositions explored even though the quantity is very small. As such removal of these LRE and HRE elements and replacement with Gd/Dy/Er would not be expected to make a material difference to the quantity of coarse particles.

It has been found that the recrystallization behaviour during a heat treatment of the alloy is improved, i.e. heat treatment for complete recrystallization is possible at lower temperature or at shorter times with less probability for excessive grain growth. The later effect in general leads to microstructures having a larger grain size which is detrimental to the mechanical properties. Use of the inventive magnesium alloy has thus an advantage in terms of processability, is more economical and improves the mechanical properties of the alloy.

It could be demonstrated that the magnesium alloy of the invention includes significantly less precipitates and has a larger grain size after extrusion compared to conventional WE alloys. It is assumed that the beneficial effects in processability contribute to the low content of elements forming intermetallic precipitates as well as point failures.

Examination of the microstructure of the inventive magnesium alloy and conventional WE43 revealed that after several deformation steps and subsequent intermediate heat treatments there were significant less and smaller precipitates in the inventive magnesium alloy than in WE43 processed in exactly the same way.

In other words, the selection of the type of RE and EIRE, present in Mg—Y—(Nd-)HRE-Zr alloy, has surprisingly led to an improvement in the formability characteristics. It is proposed, that this improvement is achieved by a reduction in hard particles (precipitated) and/or by reducing recrystallisation temperature.

It is well known, that general corrosion of magnesium alloys is affected by contaminants such as iron, nickel, copper and cobalt. This is due to the large difference in electrochemical potential between these elements and magnesium. In corrosive environments, micro galvanic cells are produced, which leads to corrosion. Addition of REs to magnesium has been reported to have some effect on corrosion of binary alloys. Until now, there does not however appear to be clear teaching, upon the effect of changing small amounts (in the region of this patent application) of RE/HRE on the corrosion performance of magnesium alloys. Surprisingly, it has been found that by selecting the RE/HRE content of Mg—Y—(Nd-)HRE-Zr, that corrosion performance was improved by a factor of approximately four. This occurred, without reducing the overall total RE/HRE content of the alloys investigated. The reduction in particles observed in Mg—Y—(Nd-)HRE-Zr alloy by reducing the less favourable HRE/RE is more than would be expected from the amounts of detrimental HRE/RE replaced by the more favourable ones.

Beside that an improvement of the corrosion resistance of the alloy in PBS (phosphate buffered saline) has been demonstrated. Samples made of the inventive alloy showed a slower degradation rate that samples made of conventional WE43. These in vitro measurements under physiological conditions were confirmed by in vivo results from animal trails with mini pigs.

In summary, the benefit of lower recrystallisation temperature and reduced particles is an improvement in ductility, and improved formability, during forming operations; thus scrap and processing time can be reduced. In addition, the corrosion performance of the material has been improved. All of the above changes are achieved, without a change in the overall RE/HRE content of the alloy compared to conventional WE43 alloys and without detriment to mechanical strength of the material.

Preferably, the content of Y in the Mg—Y—(Nd-)HRE-Zr alloy is 3.5-4.5% by weight, most preferred 3.9-4.1% by weight. Keeping the content of Y within the ranges ensures that the consistency of properties, e.g. scatter during tensile testing, is maintained.

The content of Nd in the Mg—Y—Nd-HRE-Zr alloy is 1.5-4.5% by weight, preferably 1.5-3.0% by weight, more preferred 2.0-3.0% by weight, most preferred 2.0-2.5% by weight. When the content of Nd is at least 1.5% by weight, the strength of the alloy is increased. However, when the content of Nd is above 4.5% by weight, the ductility of the alloy is deteriorated due to a limited solubility of Nd in Mg.

In addition, the content of Zr in the Mg—Y—(Nd-)HRE-Zr alloy is preferably 0.1-0.7% by weight. For magnesium-zirconium alloys, zirconium has a significant benefit of reducing the grain size of magnesium alloys, especially of the pre-extruded material, which improves the ductility of the alloy.

It has further been shown that impurities of iron and nickel are effectively controlled due to zirconium and aluminium combining with iron and nickel to form an insoluble compound. This compound is precipitated in the melting crucible and settled prior to casting [Emley et al., Principles of Magnesium Technology. Pergamon Press 1966. p. 126ff; U.S. Pat. No. 3,869,281]. Thus Zr and Al contribute to improved corrosion/degradation resistance. To ensure these effects the content of Zr should be at least 0.1% by weight while the content of Al should be less than 0.3%. Preferably, the inventive magnesium alloy includes less than 0.2% by weight Al.

A total content of Er, Gd and Dy in the Mg—Y—(Nd-)HRE-Zr alloy is preferably in the range of 0.5-1.5% by weight, more preferred 0.5-1.0% by weight.

A total content of Nd, Er, Gd and Dy in the alloy is preferably in the range of 2.0-3.5% by weight. Within this range, maintenance of ductility can be ensured.

Preferably, the inventive magnesium alloy includes Gd and Dy, especially solely Gd.

Preferably, the inventive magnesium alloy includes less than 0.02% by weight Li.

The total content of impurities in the alloy should be less than 0.3% by weight, more preferred less that 0.2% by weight. In particular, the following maximum impurity levels should be preserved:

Ce, Yb, Sm, La, Zn, Fe, Si, Cu, Mn, Ag: 0.05% individually by weight

Ni: 0.003% by weight

The processing of the biodegradable magnesium alloys has a significant effect on the processability and ductility of the material. In structural terms it has been found that an improvement in processability and/or ductility becomes noticeable when the area percentage of particles in the alloy having an average particle size in the range of 1 to 15 µm is less than 3%, and particularly less than 1.5%. Most preferred the area percentage of particles having an average size greater than 1 µm and less than 10 µm is less than 1.5%. These detectable particles tend to be brittle.

For purposes of the present disclosure, alloys are referred to as biodegradable in which degradation occurs in a physiological environment, which finally results in the entire implant or the part of the implant formed by the material losing its mechanical integrity. Artificial plasma, as has been previously described according to EN ISO 10993-15:2000 for biodegradation assays (composition NaCl 6.8 g/l. $CaCl_2$ 0.2 g/l. $KCl$ 0.4 g/l. $MgSO_4$ 0.1 g/l. $NaHCO_3$ 2.2 g/l. $Na_2HPO_4$ 0.126 g/l. $NaH_2PO_4$ 0.026 g/l), is used as a testing medium for testing the corrosion behavior of an alloy coming into consideration. For this purpose, a sample of the alloy to be assayed is stored in a closed sample container with a defined quantity of the testing medium at 37° C. At time intervals-tailored to the corrosion behaviour to be expected-of a few hours up to multiple months, the sample is removed and examined for corrosion traces in a known way.

Implants are devices introduced into the body via a surgical method and comprise fasteners for bones, such as screws, plates, or nails, surgical suture material, intestinal clamps, vascular clips, prostheses in the area of the hard and soft tissue, and anchoring elements for electrodes, in particular, of pacemakers or defibrillators. The implant is preferably a stent.

Stents of typical construction have filigree support structures made of metallic struts which are initially provided in an unexpanded state for introduction into the body and are then widened into an expanded state at the location of application.

Vascular implants, especially stents, are preferably to be designed in regard to the alloys used in such a way that a mechanical integrity of the implant is maintained for 2 through 20 weeks. Implants as an occluder are preferably to be designed in regard to the biodegradable in such a way that the mechanical integrity of the implant is maintained for 6 through 12 months. Orthopedic implants for osteosynthesis are preferably to be designed in regard to the magnesium alloy in such a way that the mechanical integrity of the implant is maintained for 6 through 36 months.

BRIEF DESCRIPTION OF THE DRAWINGS

The present disclosure is explained in greater detail in the following on the basis of exemplary embodiments and the associated drawings.

FIGS. 1A and 2A show microstructures of samples made of a conventional WE alloy after extrusion at 450° C. and after tube drawing;

FIGS. 1B and 2B show microstructures of samples made of the inventive magnesium alloy after extrusion at 450° C. and after tube drawing;

DETAILED DESCRIPTION OF THE INVENTION

Figures 3A, 3B:
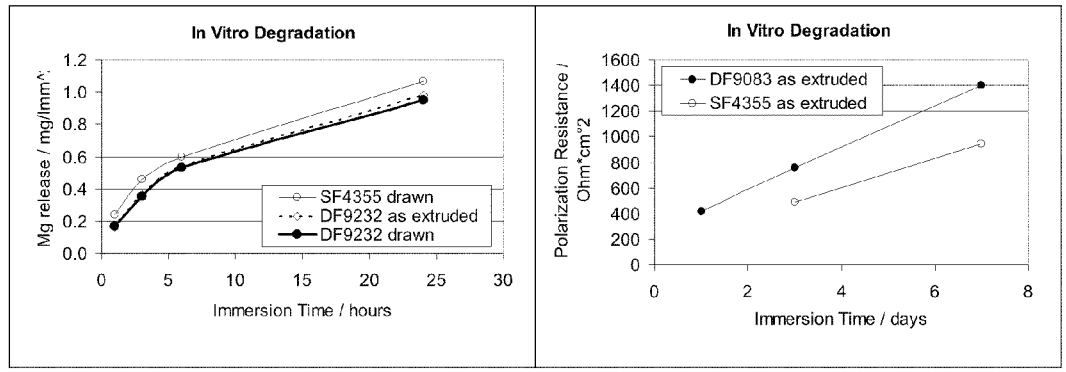
FIG. 3A is a graph demonstrating Mg release rates in PBS of samples made of a conventional WE alloy or the inventive magnesium alloy.
FIG. 3B is a graph demonstrating the polarization resistance of samples made of a conventional WE alloy or the inventive magnesium alloy.

Several melts with different alloy compositions were melted and cast, extruded and were subject to different investigation with the emphasis on the microstructure (grain size, size, fraction and composition of precipitates) and the respective thermo-mechanical properties (tensile properties, recovery and recrystallization behaviour). In general, melts were carried out according to the following casting technique:

Alloys were prepared, by melting in steel crucibles. The melt surface was protected by use of protective gas ($CO_2$/2% $SF_6$). Temperature was raised to 760-800° C. before the molten alloy was stirred to homogenise the melt chemistry. The molten alloy was then cast into a mould to achieve a billet of nominally 120 mm diameter and 300 mm length.

The billet was machined to nominally 75 mm diameter and 150-250 mm length. The billet was homogenised, by heating to approximately 525° C. for 4-8 hours.

Extrusion was carried out on a hydraulic press. The product was round bar section, with 3.2 mm to 25 mm, more typical 9.5 mm diameter. Following extrusion, approximately 300 mm of extrude, was discarded from each end of the extruded section. The remaining material was used for evaluation.

Table 2 summarises the chemical compositions, corrosion rates and tensile properties of exemplary extruded Mg—Y—Nd-HRE-Zr alloys. SF2894. SF4619 and SF4355 are comparative examples of commercially available WE alloys. Each time, two melts were produced to generate tensile data and for metallography. The yield strength (YS; or yield point) of a material is defined as the stress at which material strain changes from elastic deformation to plastic deformation, causing it to deform permanently. UTS means Ultimate Tensile Strength defined as the maximum stress a material can withstand before break. Elongation stands for elongation at fracture.

As can be seen form the data of Table 2, the inventive changes in the composition of the alloys were not detrimental to tensile properties in terms of strength, but in the case of ductility as measured by elongation, a noticeable improvement was observed where the HRE component of the alloys was rich in Gd/Dy/Er.

FIG. 1 shows microstructures of comparative sample SF2894 (FIG. 1A) and sample DF9083 (FIG. 1B) after extrusion at 450° C. For this metallographic examination of the as extruded condition the materials, SF2894 and DF9083, were melted, cast, homogenized, cut to billets and extruded to bars. Then samples were cut, embedded in epoxy resin, ground, polished to a mirror like finish and etched according to standard metallographic techniques [G Petzow, Metallographisches, keramographisches and plastographisches Ätzen, Borntraeger 2006].

FIG. 2 shows microstructures of comparative sample SF2894 (FIG. 2A) and sample DF9083 (FIG. 2B) after extrusion and subsequent tube drawing. For the metallographic examination of drawn tubes the materials the extruded bars from the previous section were deep hole drilled and cold drawn in several steps (5-20% deformation per step) with intermediate heat treatments (350° C. to 525° C. for 10 min to 48 h depending on degree of deformation and sample size) to the final tube size with a diameter of 2 mm and a wall thickness of about 0.2 mm. Then samples preparation was the same as in the previous section.

As can be seen from FIGS. 1A and 1B, the inventive magnesium alloy has significantly less precipitates and a slightly larger grain size after extrusion. The investigation further revealed in FIGS. 2A and 2B that after several deformation steps and the respective intermediate heat treatments there are significant less and smaller precipitates in sample DF9083 and that the grain size of sample DF9083 is still slightly larger than for comparative example SF2894 processed exactly the same way.

The investigation further revealed that the mechanical properties of both drawn tubes differ slightly in terms of strength (YS=160-175 MPa; UTS=240-260 MPa) but significantly in terms of scatter in the elongation at fracture (SF2894=10-20%; DF9083=18-23%). The fact that the inventive alloy reaches almost the same maximum elongation at fracture with a coarser microstructure also clearly indicates that even higher elongations at fracture are achieved by adjustment of the grain size with an appropriate recrystallization heat treatment.

In a preliminary test it could be demonstrated that the inventive magnesium alloys are less sensitive to temperature variations. In particular, the range between uniform elongation and elongation at fracture is more uniform compared to conventional magnesium alloys. The inventive alloys soften at a lower annealing temperature than conventional alloys and thus ductility is maintained at a more uniform level.

Beside the improvement of the mechanical properties and through this the improvement in processability, there was also found for the alloys of the present invention an improvement in the corrosion properties. For corrosion testing extruded bar samples were machined and tested in 5% NaCl salt fog environment for 7 days in accordance with ASTM B117. Corrosion product was removed using a boiling solution of 10% chromium trioxide solution. Weight loss of samples was determined and is expressed in mpy (mils penetration per year). The tested alloys exhibit a corrosion rate as measured according to ASTM B117 of less than 30 Mpy. Thus, it can be seen that there is an improvement in salt fog corrosion performance compared to conventional biodegradable magnesium alloys.

Since it is known that different corrosion media lead to different corrosion behaviour the corrosion resistance of the materials were in addition characterized by electrochemical impedance spectroscopy (EIS) and quantification of the Mg ion release in solutions (SBF and PBS,) simulating the actual implant environment. For EIS measurements samples of the as extruded condition were used in a conventional three electrode assembly (sample=working-, reference- and counter-electrode) and a potentiostat as described elsewhere.

The measurement of the complex resistance (polarization resistance) with electrochemical impedance spectroscopy in SBF (Simulated Body Fluid) revealed significantly higher resistances of the inventive magnesium alloy of sample DF9083 (bold symbols; see FIG. 3B) compared to the conventional magnesium alloy of sample SF4355 (plain symbols; FIG. 3B) indicating the higher corrosion resistance of the inventive extruded material.

Since it is also known that the thermo-mechanical history of materials affects the corrosion behaviour we also characterized the corrosion resistance of the materials by quantification of the Mg ion release of actual fully processed stents in PBS.

The samples for the Mg ion release tests were manufactured from drilled sleeves of the as extruded material and from drawn tubes. The sleeves and tubes were laser beam cut to the shape of stents, electro-polished, crimped on balloon catheters, sterilized and expanded into hoses of appropriate size where they were surrounded be flowing PBS. Samples from the test solution were taken a different time points and subject to quantitative Mg ion evaluation by means of a photometric procedure described elsewhere.

The measurement of Mg release from actual implants (stents) in PBS (Phosphate Buffered Saline) clearly indicates that the dissolution of material produced from drawn material of the sample DF9083 (bold symbols; see FIG. 3A) is reduced with respect to the dissolution of stents produced from drawn tubes made of comparative sample SF4355 (plain symbols; see FIG. 3A). It also clearly indicates material produced from as extruded DF9083 material (dashed line; FIG. 3A) without any further thermo-mechanical processing has a slower degradation rate than material produced from drawn SF4355 tubes (plain symbols; see FIG. 3A). It further indicates that material after severe (repetitive) thermo-mechanical processing, here tube drawing, (DF9232 drawn; bold symbols; FIG. 3A) exhibits a slower degradation rate than material produced from extruded DF9232 material (dashed line; FIG. 3A) without any further thermo-mechanical processing.

As mentioned before the actual implant environment can hardly be simulated in vitro. Therefore the most reliable test regarding the properties (biological, mechanical, corrosion) is the in vivo test in animal studies.

The study objective was to test alloy DF9232 compared to SF4355 with a view to the impact on degradation speed and tissue reactions. This study was a randomized, controlled animal study on 21 minipigs. It was aspired to implant each animal with one stent in each of the three large coronary arteries. 21 SF4355 and 42 DF9232 stents were implanted.

Follow-up investigations were performed after 2 and 4 weeks. After explantation the arteries were subjected to morphometrical and histopathological examination.

The pig was selected as the test animal for this study because it is a recognized and proved animal model for stent implantations (RS. Schwartz "Drug Eluting Stents in Preclinical Studies": Circulation, Vol. 106, 2002, p. 1867-1873: AG. Touchard and RS. Schwartz "Preclinical Restenosis Models: Challenges and Successes" Toxicologic Pathology, Vol. 34, 2006, p. 11-18). The anatomy of the pig's coronary system is very similar to that of a human. Furthermore, the expected long-term behaviour of a stent in a human can be to assessed in a pig in a comparatively short period of time as all the factors of a vascular response occur five to six times faster in the pig.

The study protocol was approved by the animal protection authorities and the animal commission. The protocol complies with the conditions and regulations of the "German Animal Protection Act (May 25, 1998)" and with the guidelines of ISO 10993-2 (Biological Assessment of Medical Products Part 2: Animal Protection Regulations).

To evaluate the influence on the degradation speed the samples from the morphometric evaluation of vessel parameters were further investigated with respect to the ratio between remaining metallic material of the stent struts and the original strut size.

Figure 4:
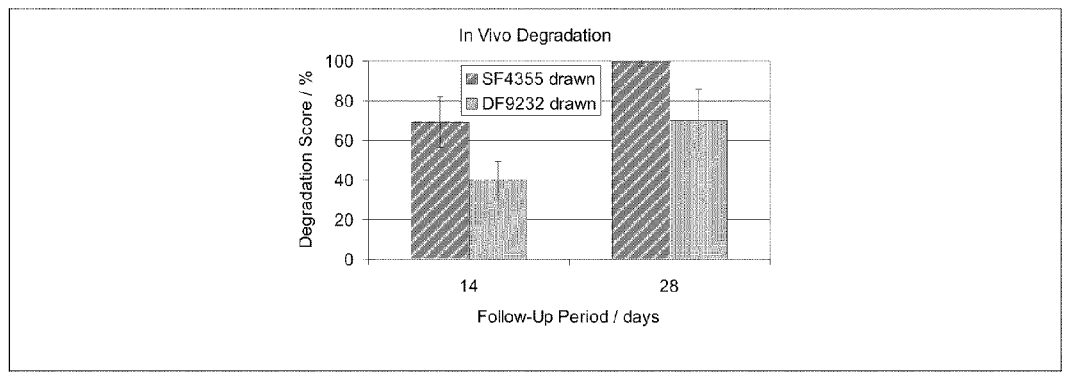
FIG. 4 demonstrates the in vivo degradation of stents made of a conventional WE alloy or the inventive magnesium alloy after 2 respectively 4 weeks after implantation.

FIG. 4 demonstrates the in vivo degradation of stents made of the conventional material of sample SF4355 and the inventive magnesium alloy of sample DF9232, each after 2 respectively 4 weeks after implantation. It can be seen that the inventive magnesium alloy of sample DF9232 exhibited significant less degradation indicated by the significant lower degradation score.

Table 3 sets out the estimated area and mean size data of particles found in a selection of alloys. The technique used was optical microscopy using commercially available software to analyse particle area and size by difference in colouration of particles. This technique does not give an absolute value, but does give a good estimation which was compared with physical measurement of random particles. Table 3 clearly illustrates a reduction in the number of detectable particles in the alloys of this invention, and these particles are likely to be brittle.

TABLE 3

| Melt Number | Area of particles as percentage of matrix (%) | Mean Diameter (microns) |
| --- | --- | --- |
| SF2894 | 5.8 | 4.3 |
| SF4619 | 3.5 | 2.6 |
| DF9520 | 1.5 | 3 |
| DF9081 | 0.1 | 0.8 |
| DF9082 | 0 | 1 |
| DF9548 | 1.1 | 1.2 |
| DF9083 | 0.7 | 2.4 |
| DF9545 | 0.5 | 1.2 |
| DF9518 | 1.7 | 2.6 |
| DF9547 | 5.3 | 2.4 |

TABLE 2

Chemical composition, corrosion rate and tensile properties of extruded Mg—Y—Nd—HRE—Zr alloys

| ID | Chemical Analysis [wt %] | | | | | | | | | | |
| --- | --- | --- | --- | --- | --- | --- | --- | --- | --- | --- | --- |
| | Y | Nd | Zr | Gd | Dy | Er | Yb | Sm | La | Ce | Li |
| SF2894 | 3.74 | 2.15 | 0.52 | 0.15 | 0.21 | 0.10 | 0.05 | 0.06 | 0.06 | 0.01 | 0.00 |
| SF4619 | 3.90 | 2.20 | 0.56 | 0.28 | 0.30 | 0.09 | 0.03 | 0.03 | 0.00 | 0.00 | 0.00 |
| SF4355 | 3.90 | 2.10 | 0.51 | 0.34 | 0.36 | 0.09 | 0.03 | 0.02 | 0.00 | 0.00 | 0.00 |
| DF9547 | 4.00 | 2.30 | 0.53 | 5.90 | 0.01 | 0.02 | 0.00 | 0.04 | 0.00 | 0.00 | 0.00 |
| DF9179 | 4.20 | 2.40 | 0.52 | 0.48 | 0.48 | 0.01 | 0.00 | 0.01 | 0.00 | 0.00 | 0.00 |
| DF9192 | 3.90 | 2.20 | 0.59 | 0.48 | 0.49 | 0.01 | 0.00 | 0.00 | 0.00 | 0.00 | 0.00 |
| DF9232 | 4.00 | 2.10 | 0.63 | 0.38 | 0.43 | 0.01 | 0.00 | 0.00 | 0.00 | 0.00 | 0.00 |
| DF9083 | 4.06 | 2.32 | 0.55 | 0.65 | 0.00 | 0.01 | 0.00 | 0.00 | 0.00 | 0.01 | 0.00 |
| DF9518 | 3.80 | 2.20 | 0.58 | 0.00 | 0.54 | 0.01 | 0.00 | 0.00 | 0.00 | 0.00 | 0.00 |
| DF9520 | 4.30 | 2.30 | 0.55 | 0.54 | 0.00 | 0.01 | 0.00 | 0.00 | 0.00 | 0.00 | 0.00 |
| DF9035 | 3.90 | 2.40 | 0.02 | 0.42 | 0.45 | 0.00 | 0.00 | 0.01 | 0.00 | 0.00 | 0.00 |
| DF9082 | 3.85 | 0.04 | 0.47 | 0.00 | 2.57 | 0.01 | 0.00 | 0.01 | 0.00 | 0.02 | 0.00 |
| DF9081 | 3.93 | 0.07 | 0.46 | 2.80 | 0.00 | 0.01 | 0.00 | 0.02 | 0.00 | 0.04 | 0.00 |
| DF9545 | 4.30 | 2.30 | 0.59 | 0.54 | 0.00 | 0.47 | 0.00 | 0.00 | 0.00 | 0.00 | 0.00 |
| DF9548 | 4.20 | 2.30 | 0.52 | 1.53 | 1.50 | 0.01 | 0.00 | 0.02 | 0.00 | 0.00 | 0.00 |

| | Chemical Analysis [wt %] | | | | Corrosion[2] [Mpy] | Tensile Properties | | |
| --- | --- | --- | --- | --- | --- | --- | --- | --- |
| | | | | | | 0.2% YS [Mpa] | UTS [Mpa] | Elong. [%] |
| ID | Al | Fe | Ni | HRE[1] | Mpy | Mpa | Mpa | % |
| SF2894 | 0.007 | 0.003 | 0.001 | 0.46 | 40 | n/m | n/m | n/m |
| SF4619 | 0.01 | 0.002 | 0.001 | 0.67 | 43 | 209 | 298 | 19 |
| SF4355 | 0.01 | 0.003 | 0.001 | 0.79 | n/m | 218 | 286 | 19 |
| DF9547 | 0.01 | 0.002 | 0.001 | 5.93 | 13 | 254 | 333 | 17.5 |
| DF9179 | 0.01 | 0.002 | 0.001 | 0.97 | 12 | 202 | 290 | 25 |
| DF9192 | 0.01 | 0.002 | 0.001 | 0.98 | 9 | 208 | 286 | 28 |
| DF9232 | 0.01 | 0.003 | 0.001 | 0.82 | 7 | 233 | 296 | 25 |
| DF9083 | 0.006 | 0.002 | 0.001 | 0.66 | 10 | 193 | 283 | 27 |
| DF9518 | 0.01 | 0.002 | 0.001 | 0.55 | 8 | 204 | 279 | 25 |
| DF9520 | 0.01 | 0.002 | 0.001 | 0.55 | 8 | 212 | 292 | 24 |
| DF9035 | 0.24 | 0.001 | 0.001 | 0.87 | 6 | 187 | 263 | 26 |
| DF9082 | 0.005 | 0.003 | 0.001 | 2.58 | 11 | 150 | 244 | 24 |
| DF9081 | 0.008 | 0.003 | 0.001 | 2.81 | 11 | 152 | 250 | 25 |
| DF9545 | 0.01 | 0.002 | 0.001 | 1.01 | 8 | 198 | 286 | 26 |
| DF9548 | 0.01 | 0.002 | 0.001 | 3.04 | 12 | 223 | 307 | 24 |

[1]Sum of (only) Gd, Dy, and Er

What is claimed is:

1. A vascular implant made in total or in parts of a biodegradable magnesium alloy consisting essentially of:
Y: from about 3.8% to about 4.0% by weight,
Nd: from about 0.04% to about 0.07% by weight,
Gd: 0 to about 2.8% by weight,
Dy: 0 to about 2.57% by weight,
Er: about 0.01% by weight, Zr: from about 0.46% to about 0.47% by weight;
under the condition that:
a) a total content of Er, Gd and Dy is about 2.58% to about 2.81% by weight, and
b) a total content of Nd, Er, Gd and Dy is about 2.62% to about 2.88% by weight;
the balance being magnesium and incidental impurities, optionally including Al or Li, up to a total of 0.3% by weight;
wherein the area percentage of particles in the alloy having an average particle size in the range of 1 to 15 µm is less than 3%.

2. The vascular implant of claim 1, wherein the vascular implant is a stent.

3. The vascular implant of claim 1, wherein,
Y is 3.93% by weight,
Nd is 0.07% by weight,
Gd is 2.8% by weight,
Dy is 0% by weight,
Er is 0.01% by weight, and
Zr is 0.46% by weight.

4. The vascular implant of claim 1, wherein
Y is 3.85% by weight,
Nd is 0.04% by weight,
Gd is 0.0% by weight,
Dy is 2.57% by weight,
Er is 0.01% by weight, and
Zr is 0.47% by weight.

5. A method of manufacturing a vascular implant, comprising:
providing a biodegradable magnesium alloy according to claim 1, and forming the vascular implant up to a total of 0.3% by weight of the alloy.

6. The method of claim 5, wherein the vascular implant is a stent.

7. A vascular implant made in total or in parts of a biodegradable magnesium alloy consisting essentially of:
Y is about 4.0% by weight,
Nd is about 2.3% by weight,
Gd is about 5.9% by weight,
Dy is about 0.01% by weight,
Er is about 0.02% by weight,
Zr is about 0.53% by weight; and
the balance being magnesium and incidental impurities, optionally including Al or Li, up to a total of 0.3% by weight;
wherein the area percentage of particles in the alloy having an average particle size in the range of 1 to 15 µm is less than 3%.

8. The vascular implant of claim 7, wherein the vascular implant is a stent.

* * * * *